US011584797B2

(12) United States Patent
Burger

(10) Patent No.: US 11,584,797 B2
(45) Date of Patent: Feb. 21, 2023

(54) INHIBITION OF CCL5 LIGAND BINDING TO CCR5 RECEPTOR AND ALTERATION OF CCR5/CCL5 AXIS SIGNALING IN INFLAMMATION, CANCER, AUTOIMMUNE, AND OTHER CONDITIONS

(71) Applicant: CytoDyn Inc., Vancouver, WA (US)

(72) Inventor: Denis R. Burger, Vancouver, WA (US)

(73) Assignee: Cytodyn Inc., Vancouver, WA (US)

( * ) Notice: Subject to any disclaimer, the term of this patent is extended or adjusted under 35 U.S.C. 154(b) by 18 days.

(21) Appl. No.: 15/737,706

(22) PCT Filed: Jun. 23, 2016

(86) PCT No.: PCT/US2016/039016
§ 371 (c)(1),
(2) Date: Dec. 18, 2017

(87) PCT Pub. No.: WO2016/210130
PCT Pub. Date: Dec. 29, 2016

(65) Prior Publication Data
US 2019/0002571 A1    Jan. 3, 2019

Related U.S. Application Data

(60) Provisional application No. 62/183,335, filed on Jun. 23, 2015.

(51) Int. Cl.
| | | |
|---|---|---|
| *C07K 16/28* | (2006.01) |
| *A61K 31/439* | (2006.01) |
| *A61P 37/06* | (2006.01) |
| *A61P 31/12* | (2006.01) |
| *A61K 39/00* | (2006.01) |
| *A61P 25/28* | (2006.01) |

(52) U.S. Cl.
CPC ........ *C07K 16/2866* (2013.01); *A61K 31/439* (2013.01); *A61P 25/28* (2018.01); *A61P 31/12* (2018.01); *A61P 37/06* (2018.01); *A61K 2039/505* (2013.01); *C07K 2317/76* (2013.01)

(58) Field of Classification Search
CPC . C07K 2317/76; C07K 16/2866; A61P 37/06; A61K 2039/505
See application file for complete search history.

(56) References Cited

U.S. PATENT DOCUMENTS

| | | |
|---|---|---|
| 7,060,273 B2 | 6/2006 | Olson et al. |
| 8,361,736 B2 | 1/2013 | Majeti et al. |
| 9,730,960 B2 | 8/2017 | McFadden et al. |
| 10,023,840 B2 | 7/2018 | Sykes et al. |
| 2002/0019345 A1 | 2/2002 | Hancock |
| 2003/0228306 A1 | 12/2003 | Olson et al. |
| 2007/0026441 A1* | 2/2007 | Olson .................. C12Q 1/701 435/5 |
| 2008/0241135 A1 | 10/2008 | Olson et al. |
| 2010/0178290 A1 | 7/2010 | Olson et al. |
| 2013/0216525 A1 | 8/2013 | Chen |
| 2013/0216526 A1 | 8/2013 | Olson et al. |
| 2013/0324552 A1 | 12/2013 | Wilson et al. |
| 2014/0377259 A1* | 12/2014 | Olson .............. A61K 39/39541 424/133.1 |
| 2017/0049884 A1 | 2/2017 | Montgomery |
| 2019/0014758 A1 | 1/2019 | Burger |
| 2019/0016810 A1 | 1/2019 | Burger |
| 2019/0085086 A1 | 3/2019 | Maddon et al. |

FOREIGN PATENT DOCUMENTS

| | | | |
|---|---|---|---|
| CN | 1956720 A | 5/2007 |
| CN | 103764228 A | 4/2014 |
| WO | 2003/000928 A2 | 1/2003 |
| WO | 03/072766 | 9/2003 |
| WO | WO-2005016226 A2 * | 2/2005 | ............ A61K 31/00 |
| WO | 2010/126278 A2 | 11/2010 |
| WO | 2013/024022 A1 | 2/2013 |
| WO | WO-2014085808 A1 * | 6/2014 | ............ A61K 31/55 |
| WO | 2015/126892 A1 | 8/2015 |
| WO | 2016/029049 A1 | 2/2016 |
| WO | 2016/123334 A1 | 8/2016 |
| WO | 2016/210130 | 12/2016 |
| WO | 2018/209301 A1 | 11/2018 |

OTHER PUBLICATIONS

Bowie et al. Science, 1990, 247:1306-1310 (Year: 1990).*
Burgess et al. (Journal of Cell Biology; 111:2129-2138, 1990 (Year: 1990).*
Lazar et al. Molecular Cellular Biology, 8:1247-1252, 1988 (Year: 1988).*
Paul. Fundamental Immunology, 3rd Edition, Raven Press, New York, Chapter 8, pp. 292-295, 1993 (Year: 1993).*
MacCallum et al. Journal of Molecular Biology, 262:732-745, 1996 (Year: 1996).*
Casset et al. Biochemical and Biophysical Research Communications, 307:198-205, 2003 (Year: 2003).*
Vajdos et al. Journal of Molecular Biology, Jul. 5, 2002;320(2):415-28 (Year: 2002).*
Ferrara et al. mABs, 2015; 7(1): 32-41 (Year: 2015).*
Gilliam et al. Journal of Translational Medicine, 2010; 9(Suppl 1):59; 1-14 (Year: 2010).*

(Continued)

*Primary Examiner* — Vanessa L. Ford
*Assistant Examiner* — Sandra Dillahunt
(74) *Attorney, Agent, or Firm* — Seed IP Law Group LLP

(57) ABSTRACT

Methods for the therapeutic use of competitive inhibitors of the CCR5/CCL5 axis that express antagonist activity for RANTES (CCL5) for immunomodulatory treatment of subjects in need thereof. The competitive inhibitors may not have CCL5 agonist activity and can be used to inhibit, interrupt, block, mitigate, slow the progress of, and/or treat inflammation and/or various other CCR5/CCL5 axis signaling dependent down-stream activities associated with transplantation, including graft versus host disease, autoimmune disorders, infectious agents, chronic inflammation, and cancer, etc.

11 Claims, 6 Drawing Sheets

(56) References Cited

OTHER PUBLICATIONS

O'Shaughnessy et al. Elevation of Intracellular Cyclic AMP in Alloreactive CD4+ T Cells Induces Alloantigen-Specific Tolerance That Can Prevent GVHD Lethality In Vivo. Biology of Blood and Marrow Transplantation 13:530-542 (2007) (Year: 2007).*
Murai et al. Active participation of CCR5+CD8+ T lymphocytes in the pathogenesis of liver injury in graft-versus-host disease. JCI, 1999; 104(1):49-57) (Year: 1999).*
O'Shaughnessy et al. (Biology of Blood and Marrow Transplantation 13:530-542 (2007) (Year: 2007).*
Olson et al. Differential Inhibition of Human Immunodeficiency Virus Type 1 Fusion, gp120 Binding, and CC-Chemokine Activity by Monoclonal Antibodies to CCR5. Journal of Virology, 1999, 73(5): 4142-4155 (Year: 1999).*
Lopalco et al. Natural anti-CCR5 antibodies in HIV-infection and -exposure. Journal of Translational Medicine 2010, 9(Suppl 1):S4) (Year: 2010).*
Palmer et al. Chemokine ReceptorCCR5 Mediates Allo-Immune Responses in Graft-vs-Host Disease. Biol Blood Marrow Transplant. Mar. 2010 ; 16(3): 311-319 (Year: 2010).*
Akkina, "Human immune responses and potential for vaccine assessment in humanized mice," *Current Opinion in Immunology* 25(3):403-409, 2013. (11 pages).
Burger et al., "PRO 140 Monoclonal Antibody to CCR5 Prevents Acute Xenogeneic Graft-versus-Host Disease in NOD-*scid* IL-2Ry$^{null}$ Mice," *Biology of Blood and Marrow Transplantation* 24(2):260-266, 2018.
CytoDyn Inc., "Study of PRO 140 for Prophylaxis of Acute GVHD in Patients Undergoing RIC Allogenic Stem-Cell Transplantation (GVHD)," dated Aug. 15, 2018, URL=https://clinicaltrials.gov/ct2/show/NCT02737306, download date Aug. 16, 2018, 7 pages.
Gilliam et al., "Clinical use of CCR5 inhibitors in HIV and beyond," *Journal of Translational Medicine* 9(Suppl. 1):S9, 2010. (14 pages).
Huang et al., "Engineered Bispecific Antibodies with Exquisite HIV-1-Neutralizing Activity," *Cell* 165(7):1621-1631, 2016. (26 pages).
Moy et al., "Clinical and immunologic impact of CCR5 blockade in graft-versus-host disease prophylaxis," *Blood* 129(7):906-916, 2017.
Murai et al., "Active participation of CCR5$^{+CD8+}$ T lymphocytes in the pathogenesis of liver injury in graft-versus-host disease," *The Journal of Clinical Investigation* 104(1):49-57, 1999.
Murga et al., "Potent Antiviral Synergy between Monoclonal Antibody and Small-Molecule CCR5 Inhibitors of Human Immunodeficiency Virus Type 1," *Antimicrobial Agents and Chemotherapy* 50(10):3289-3296, 2006.
Palmer et al., "Chemokine Receptor CCR5 Mediates Allo-Immune Responses in Graft-vs-Host Disease," *Biology of Blood and Marrow Transplantation* 16(3):311-319, 2010. (14 pages).
Banerjee et al. "Transcriptional regulation of the chemokine co-receptor CCR5 by the cAMP/PKA/CREB pathway," Biomed Pharmacother. May 30, 2011, vol. 65, No. 4, pp. 1-12.
Wikipedia, "Human body weight," URL=https://en.wikipedia.org/wiki/Human_body_weight, version modified Jul. 25, 12 pages, 2020.
Bruhl et al., "Depletion of CCR5-Expressing Cells with Bispecific Antibodies and Chemokine Toxins: A New Strategy in the Treatment of Chronic Inflammatory Diseases and HIV," *J Immunol* 166:2420-2426, 2001.
De Groot et al., "Expression of the chemokine receptor CCR5 in psoriasis and results of a randomized placebo controlled trial with a CCR5 inhibitor," *Arch Dermatol Res* 299:305-313, 2007.
Desmetz et al., "The strength of the chemotactic response to a CCR5 binding chemokine is determined by the level of a cell surface CCR5 density," *Immunology* 119:551-561, 2006.
Pham et al., "CCL5, CCR1 and CCR5 in murine glioblastoma: immune cell infiltration and survival rates are not dependent on individual expression of either CCR1 or CCR5," *J Neuroimmunol.* 246(1-2):10-17, 2012 (NIH Public Access Author Manuscript, available in PMC May 15, 2013)(17 pages).
Rossi et al., "In vitro effect of anti-human immunodeficiency virus CCR5 antagonist maraviron on chemotactic activity of monocytes, macrophages and dendritic cells," *Clinical & Experimental Immunology*:184-190, 2011.
Aldinucci et al., "The Inflammatory Chemokine CCL5 and Cancer Progression," *Mediators of Inflammation* 2014(292376):1-12, 2014.
Anonymous, "NCT00613379: PRO 140 by IV Administration in Adults with HIV-1 Infection," *US National Library of Medicine, Clinical Trials.gov*, 5 pages. Accessed: Aug. 7, 2019.
Blanco et al., "Off-label use of maraviroc in clinical practice," *Expert Ref. Anti Infect. Ther.* 14(1):5-8, 2016.
Castor et al., "The role of chemokines in mediating graft versus host disease: opportunities for novel therapeutics," *Front. Pharm.* 3:1-13, 2012.
Fleishaker et al., "Maraviroc, a chemokine receptor-5 antagonist, fails to demonstrate efficacy in the treatment of patients with rheumatoid arthritis in a randomized, double-blind placebo-controlled trial," *Arthritis Research & Therapy* 14:R11, 2012. (11 pages).
Jacobson et al., "Anti-HIV-1 Activity of Weekly or Biweekly Treatment with Subcutaneous PRO 140, a CCR5 Monoclonal NnlAtioAy," *Journal of Infectious Diseases* 201(10):1481-1487, 2010.
Latinovic et al., "Synergistic inhibition of R5 HIV-1 by maraviroc and CCR5 antibody HGS004 in primary cells: implications for treatment and prevention," *AIDS* 25(9):1232-1235, 2011.
Lemos et al., "Quantification of peripheral blood CD 34$^+$ cells prior to stem cell harvesting by leukapheresis: a single center experience," *Hematology, Transfusion and Cell Therapy* 40(3):213-218, 2018.
Murai et al., "Peyer's patch is the essential site in initiating murine acute and lethal graft-versus-host reaction," *Nature Immunol.* 4(2): 154-160, 2003.
Olson et al., "Differential Inhibition of Human Immunodeficiency Virus Type 1 Fusion, gp120 Binding, and CC-Chemokine Activity by Monoclonal Antibodies to CCR5," *Journal of Virology* 73(5):4145-4155, 1999.
Petit et al., "Gene transfer of two entry inhibitors protects CD4$^+$ T cell from HIV-1 infection in humanized mice," *Gene Therapy* 23:144-150, 2016.
Reshef et al., "Blockade of Lymphocyte Chemotaxis in Visceral Graft-versus-Host Disease," *N. Engl. J. Med* 367:135-145, 2012.
Shimizu et al., "RNAi-Mediated CCR5 Knockdown Provides HIV-1 Resistance to Memory T Cells in Humanized BLT Mice," *Mol. Therapy-Nucleic Acids* 4:e227, 2015.
Swan et al., "T-cell protection and enrichment through lentiviral CCR5 intrabody gene delivery," *Gene Therapy* 13:1480-1492, 2006.
Tang et al., "CCR5 blockade combined with cyclosporine A attenuates liver GVHD by impairing T cells function," *Inflamm. Res.* 65:917-924, 2016.
Yuan et al., "Prophylaxis of acute graft-versus-host disease by CCR5 blockade combined with cyclosporine A in murine model," *Inflamm. Res.* <64:137-144, 2015.
Anonymous, "Guidance for Industry, Estimating the Maximum Safe Starting Dose in Initial Clinical Trials for Therapeutics in Adult Healthy Volunteers," US FDA Publication (Jul. 2005).
Bruck et al., "Impact of bone marrow-derived mesenchymal stromal cells on experimental xenogeneic graft-versus-host disease," *Cytotherapy* 15:261-219 (2013).
Clark et al., "Discover and Development of Janus Kinase (JAK) Inhibitors for Inflammatory Diseases," *J. Med. Chem.* 57(12):5023-5038 (2014).
Foote, "Isomeric Antibodies," *Science* 299(5611):1327-1328 (2003).
Gong et al., "Candidate Antibody-Based Therapeutics Against HIV-1," *Biodrugs* 26(3):143-162 (2012).
Guido et al., "Virtual Screening and Its Integration with Modem Drug Design Technologies," *Curr Med Chem.* 15(1)37-46 (2008).
Jekle et al., "Epitope Switching as a Novel Escape Mechanism of HIV to CCR5 Monoclonal Antibodies," *Antimicrob. Agents Chemother.* 54(2):734-741 (2010).

(56) References Cited

OTHER PUBLICATIONS

NCI Thesaurus Code Code C137824, Leronlimab (2021).
Morrison et al., "Chemokine-receptor upregulation and disease severity in Respiratory Syncytial Vims infection," *Clinical Immunology* 128:85-93 (2008).
Ness et al., "CCR5 antagonists: the answer to inflammatory disease?" *Expert Opin. Ther. Patents* 16(8): 051-1065 (2006).
U.S. Appl. No. 15/119,103, filed Aug. 15, 2016, Use of Anti-CCR5 Antibodies in Graft Versus Host Disease.
U.S. Appl. No. 15/977,929, filed May 11, 2018, Methods for Treating or Preventing Graft-Versus-Host Disease Involving the Administration of Anti-CCR5 Receptor Agents.
U.S. Appl. No. 15/977,933, filed May 11, 2018, Humanized Mouse Model.

\* cited by examiner

INHIBITION OF CCL5 LIGAND BINDING TO CCR5 RECEPTOR AND ALTERATION OF CCR5/CCL5 AXIS SIGNALING IN INFLAMMATION, CANCER, AUTOIMMUNE, AND OTHER CONDITIONS

CROSS-REFERENCE TO RELATED APPLICATIONS

The present application claims priority to U.S. Provisional Patent Application No. 62/183,335, filed on Jun. 23, 2015, the contents of which are fully incorporated herein.

FIELD OF THE INVENTION

The present invention relates to competitive inhibitors to the CCR5 receptor and the use of such competitive inhibitors, such as monoclonal antibodies (including, but not limited to, PRO 140), fragments or subunits of same, proteins, small molecules, or conjugates of any of the above, of the CCL5 ligand/CCR5 receptor axis that express antagonist activity for RANTES (CCL5), MIP1-alpha (CCL3), and MIP1-beta (CCL4) in the fields of transplantation, including graft versus host disease (GvHD), autoimmune disorders (Multiple Sclerosis (MS), Lupus, psoriasis, liver disease, Crohn's Disease, Inflammatory bowel disease, etc.), infectious agents, chronic inflammation, and cancer, including, but not limited to, breast cancer, prostate cancer, etc. The competitive inhibitors of the present invention may be used to inhibit, interrupt, block, mitigate, dampen, slow the progress of, and/or treat inflammation or various other CCR5/CCL5 axis signaling dependent down-stream activities associated with GvHD, autoimmune disorders, infectious agents, chronic inflammation, and cancer.

The competitive inhibitors contemplated for this invention may or may not have CCL5 ligand/CCR5 receptor axis agonist activity. It is noted, however, that the present inventor has determined that PRO 140 is not indicated to have CCL5 ligand/CCR5 receptor axis agonist activity. Accordingly, PRO 140, or fragments, parts, or derivatives thereof, may be particularly useful for this invention.

BACKGROUND

Inflammation may occur in response to trauma, chemical or physical injury, autoimmune responses, infectious agents, cancer, etc. Inflammation is an important component of innate immunity and is necessary for priming adaptive immunity and for the effecter phase of the immune response. Soluble mediators, such as chemokines, are shown to play an important role in driving the various components of inflammation, especially leukocyte influx.

Chemokines bind to their receptors which are expressed on many cell types, including, for example, leukocytes, endothelial cells, fibroblasts, epithelial, smooth muscle and parenchymal cells. Chemokines play an important role in leukocyte biology, by controlling cell recruitment and activation in basal and in inflammatory circumstances. In addition, because chemokine receptors are expressed on other cell types, chemokines have multiple other roles, including angiogenesis, tissue and vascular remodeling, pathogen elimination, antigen presentation, leukocyte activation and survival, chronic inflammation, tissue repair/healing, fibrosis, embryogenesis, tumorigenesis, etc.

CCL5 (C-C chemokine ligand 5), an inflammatory chemokine also known as regulated upon activation and normal T cell expressed and secreted (RANTES), plays an important role in these immunologic mechanisms. CCL5 acts as a key regulator of T-cell migration to inflammatory sites, directing migration of T cells to damaged or infected sites. CCL5 also regulates T-cell differentiation. Many biologic effects of chemokines are mediated by their interaction with chemokine receptors on cell surfaces. In the present invention, the most relevant known receptor for CCL5 is the CCR5 receptor; however, CCR1 and CCR3 are also known CCL5 receptors and CCR4 and CD44 are auxiliary receptors. Tamamis et al., *Elucidating a Key Anti-HIV-1 and Cancer-Associated Axis: The Structure of CCL5 (Rantes) in Complex with CCR5*, SCIENTIFIC REPORTS; 4:5447 (2014).

Inflammatory chemokines have long been viewed mainly as indispensable "gate keepers" of immunity and inflammation. However, recent research indicates that, for example, cancer cells subvert the normal chemokine system and these molecules and their receptors become important constituents of the tumor microenvironment with very different ways to exert tumor-promoting roles. While the CCR5 receptor and the CCL5 ligand have been detected in some hematological malignancies, lymphomas, and a great number of solid tumors, extensive studies on the role of the CCL5 ligand/CCR5 receptor axis have only been performed only in a limited number of cancers. Aldinucci et al., *The Inflammatory chemokine CCL5 and Cancer Progression*, MEDIATORS OF INFLAMMATION, vol. 2014, article ID 292376, 12 pages.

The CCR5 receptor is a C-C chemokine G-coupled protein receptor expressed on lymphocytes, monocytes, macrophages, dendritic cells, a subset of T cells, etc. The CCR5 receptor spans the cellular plasma membrane seven times in a serpentine manner. The extracellular portions represent potential targets for HIV-inhibitory mAbs and comprise an amino-terminal domain (Nt) and three extracellular loops (ECL1, ECL2, and ECL3). The extracellular portions of CCR5 comprise just 90 amino acids distributed over four domains. The largest of these domains are at the Nt and ECL2 at approximately 30 amino acids each. Olson et al., *CCR5 Monoclonal Antibodies for HIV-1 Therapy*, CURR. OPIN. HIV AIDS, March; 4(2): 104-111 (2009).

The formation of the CCRL ligand and CCR5 receptor complex causes a conformational change in the receptor that activates the subunits of the G-protein, inducing signaling and leading to changed levels of cyclic AMP (cAMP), inositol triphosphate, intracellular calcium and tyrosine kinase activation. These signaling events cause cell polarization and translocation of the transcription factor NF-kB, which results in the increase of phagocytic ability, cell survival, and transcription of proinflammatory genes. Once G-protein dependent signaling occurs, the CCL5/CCR5 receptor complex is internalized via endocytosis.

A complete complex structure of CCL5 in complex with CCR5 was recently computationally derived. It is reported that the 1-15 residue moiety of CCL5 is inserted into the CCR5 binding pocket; the 1-6 N-terminal domain of CCL5 is buried within the transmembrane region of CCR5, and the 7-15 residue moiety of CCL5 is predominantly encompassed by the N-terminal domain and extracellular loops of CCR5. CCL5 residues Ala16, Arg17 and additional residues of the 24-50 residue moiety interact with the upper N-terminal domain and extracellular loop interface of CCR5. It is further reported that the integrity of the amino terminus of CCL5 is crucial to receptor binding and cellular activation. Further, it has been reported that CCL5 and HIV-1 primarily interact with mostly the same CCR5 residues, and share the same chemokine receptor binding pocket. See Tamamis et al., *Elucidating a Key Anti-HIV-1 and Cancer-Associated Axis: The Structure of CCL5 (Rantes) in Complex with*

CCR5, SCIENTIC REPORTS; 4:5447 (2014). It is also separately reported that chemokines, such as the CCL5 ligand, principally bind the CCR5 receptor through ECL2. Olson et al., *CCR5 Monoclonal Antibodies for HIV-1 Therapy*, CURR. OPIN. HIV AIDS, March; 4(2): 104-111 (2009).

Evidence suggests that CCL5/CCR5 axis signaling may be preferentially activated in certain types of cancers, for example breast and prostate cancers, and that such signaling facilitates disease progression. Exploratory efforts using anti-CCR5 binding agents to alter CCL5/CCR5 signaling in connection with some cancer types have been made. Sicoli et al., *CCR5 Receptor Antagonists Block Metastasis to Bone of v-Src Oncogene-Transformed Metastatic Prostate Cancer Cell Lines*, CANCER RES. 74(23), (2014); Velasco-Velizquez et al., *The CCL5/CCR5Axis Promotes Metastasis In Basal Breast Cancer*, ONCOIMMUNOLOGY, vol. 2, issue 4 (2013); and Velasco-Velázquez et al., *CCR5Antagonis Blocks Metastasis of Basal Breast Cancer Cells*, CANCER RES. 72(15), (2012).

Various compounds exist that inhibit, interrupt, block, alter, or modify the CCR5/CCL5 receptor/ligand axis (i.e., CCR5 receptor/CCL5 ligand axis). Many of these compounds have been developed for the treatment of HIV-1, which also binds with the CCR5 receptor and is known to share some binding commonalities with CCL5. Such compounds include extracellular or cell transmembrane CCR5 binding agents such as, for example, PRO 140 (extracellular) and maraviroc (transmembrane), and other compounds such as vicriviroc, aplaviroc, SCH-C, TAK-779, and antibodies such as PA14, 2D7, RoAb13, RoAb14, 45523, etc. It has been found that the most potently antiviral anti-CCR5 monoclonal antibodies including, for example, PRO140, bind CCR5 receptor amino acid residues in EL2 alone or in combination with Nt residues. It has also been determined that the CCR5 receptor binding sites for anti-CCR5 monoclonal antibodies are distinct from small-molecule CCR5 antagonists. That is, available small-molecule CCR5 antagonists, such as maraviroc, bind the hydrophobic cavity formed by the transmembrane helices, i.e., not the extracellular Nt or loop regions. The amino acid residue E283 in the seventh transmembrane region has been specifically identified as a principle site or interaction for small molecules, and maraviroc and vicriviroc were found to bind to identical sets of CCR5 receptor amino acids. Olson et al., *CCR5 Monoclonal Antibodies for HIV-1 Therapy*, CURR. OPIN. HIV AIDS, March; 4(2): 104-111 (2009).

It has also been reported, however, that the CCL5 ligand and maraviroc dock on the CCR5 receptor by sharing two receptor sites: the Nt and the ECL2, and that synthetic CCL5-derived peptides may also be used to block the CCR5 receptor. Secchi et al., *Combination of the CCL5-Derived Peptide R4.0 with Different HIV-1 Blockers Reveals Wide Target Compatibility and Synergic Cobinding to CCR5*, ANTIMICROBIAL AGENTS AND CHEMOTHERAPY, pp. 6215-6223; October (2014).

In vitro studies to investigate the effects of CCR5 receptor blockade by maraviroc on activated human T cells on potential immunological mechanisms have been conducted. It was found that blocking CCR5 by maraviroc not only can block CCR5 and CCR2 internalization processes induced by CCL5 and CCL2, but can also inhibit T cell chemotactic activities toward their cognate ligands, respectively. Further, blocking CCR5 with maraviroc at high doses tends to decrease production of TNF-α and IFN-γ. It was also noted that the effect of maraviroc on CCR5 was temporary and reversible. Yuan et al., *In Vitro Immunological Effects of Blocking CCR5 on T Cells*, INFLAMMATION, vol. 38, no. 2, (2015); see Arberas et al., *In vitro effects of the CCR5 inhibitor maraviroc on human T cell function*, J. ANTIMICROB. CHEMOTHER., 68: 577-586 (2013).

There exists a need, however, for improved competitive inhibitors to the CCR5 receptor and methods of use that can be used to inhibit, dampen, interrupt, block, alter, or modify the CCR5/CCL5 receptor/ligand axis for therapeutic purposes without triggering, or that reduce the impact of, unintended side effects. Further, there is a need for such competitive inhibitors to the CCR5 receptor and methods of use that cause fewer and less severe side effects, are longer-lasting, and facilitate improved patient compliance due to decreased dosing demands and improved patient experience (due to fewer undesirable side effects), including side effects caused by the competitive inhibitor itself.

Optimal therapeutic modalities using the CCL5/CCR5 axis as a therapeutic target will need to accommodate two opposing demands: the need to inhibit the detrimental involvement of CCL5 and CCR5 in specific malignant diseases while protecting their potentially beneficial activities in immunity.

INVENTION SUMMARY

The present invention is directed to methods of use and treatment using competitive inhibitors to the CCR5 receptor that blunt, inhibit, dampen, reduce, or block the effects of CCL5 binding on the CCL5 receptor. The present invention comprises competitive inhibitors to the CCR5 receptor that blunt, inhibit, dampen, reduce, or block the effects of CCL5 binding to the CCR5 receptor to decrease cAMP levels. The present invention also comprises competitive inhibitors to the CCR5 receptor that blunt, inhibit, dampen, reduce, or block cell migration otherwise induced by CCL5 binding to the CCR5 receptor. The competitive inhibitors to the CCR5 receptor of the present invention may or may not have CCL5 agonist activity upon binding to the CCR5 receptor. Preferred competitive inhibitors to the CCR5 receptor of the present invention do not have CCL5 agonist activity upon binding to the CCR5 receptor.

In a preferred embodiment, the competitive inhibitors to the CCR5 receptor of the present invention when bound to the CCR5 receptor do not have detectable CCL5 agonist activity (in terms of decreased cAMP measurements or induced cell migration) and at the same time stymie the effects of CCL5 ligands bound to CCR5 receptors. That is, in an embodiment of the present invention, the competitive inhibitors to the CCR5 receptor do not have independent CCL5 agonist activity.

The competitive inhibitors to the CCR5 receptor of the present invention may cause therapeutic effect in a dose dependent manner. Accordingly, it is contemplated that the amount of active agent administered to a subject may be adjusted to meet their immunomodulatory needs, whether these are of minor, moderate, or severe nature.

In a particularly preferred embodiment, the competitive inhibitor of the CCR5 receptor is PRO 140, or an isomer thereof, or a fragment, or derivative of PRO 140, any PRO 140 isomer, or fragment thereof. In this embodiment, the competitive inhibitor has no, or no detectable, CCL5 agonist activity when bound to the CCR5 receptor and acts to down-regulate downstream effects caused by CCL5 ligand and CCR5 receptor binding. Specifically, such downstream effects may relate to one or both of CCL5 ligand induced decreases in cAMP levels or increases in cell migration.

Potential clinical applications of using the competitive inhibitor of the CCR5 receptor of the present invention to interfere with the CCR5 receptor and the CCL5 ligand axis are numerous. Such potential applications include diseases with an inflammatory component namely, respiratory tract infections (e.g., RSV, SARS), neuroinflammation (e.g., WNV, HSV, CMV), liver infections (e.g., HCV), asthma, autoimmunity (e.g., MS, Lupus, liver disease, psoriasis, Crohn's Disease, Inflammatory bowel disease, etc.), atherosclerosis, angiogenesis and cancer (e.g., prostate, breast, melanoma, gastric, colon, ovarian, etc.), fibrosis and transplant rejection and GvHD. Methods and compounds of the present invention may also be used in connection with transplantation including GvHD, autoimmunity (e.g., MS, Lupus, Psoriasis, autoimmune liver disease, etc.), inflammation in respiratory viral diseases (e.g., RSV, SARS), other viral diseases (e.g., HCV, CMV, WNV), infectious agents, cancer applications for angiogenesis and unlocking Treg suppression of antitumor CTLs, and atherosclerosis and fibrosis. As indicated here, the interaction between the CCL5 ligand and the CCR5 receptor is implicated in several disease states.

Various CCR5 receptor binding agents are known. Competitive binding studies involving the CCR5 receptor and various anti-CCR5 binding agents including its natural ligand CCL5, and PRO 140 and maraviroc demonstrate that each of these components has a different binding capacity, and each binds to one or more distinct portions of the CCR5 receptor. PRO 140 binds to extracellular portions of the CCR5 receptor and, as exemplified below, effectively diminishes the downstream immunomodulatory effects of CCL5 binding on the CCL5 receptor. Also, unlike maraviroc, PRO 140 is shown to have no CCL5 receptor agonist activity when bound to CCR5 with respect to cAMP levels or cell migration. Accordingly, PRO 140 is shown to provide an advantageous contribution to the art and gives rise to new uses for this CCR5 receptor competitive inhibitor to inhibit, interrupt, block, mitigate, dampen, slow the progress of, and/or therapeutically treat conditions resulting, in whole or in part, from the downstream immunomodulatory effects induced by CCL5 ligand binding on the CCL5 receptor. Particularly, here the inventors provide evidence supporting methods of using the CCR5 receptor competitive inhibitors of the present invention to stymie the activity of naturally occurring CCL5 without giving rise to unintended downstream immunomodulatory effects caused by the CCR5 receptor competitive inhibitor itself, at least with respect to cAMP levels or cell migration.

DETAILED DESCRIPTION OF THE INVENTION

Figure 1:
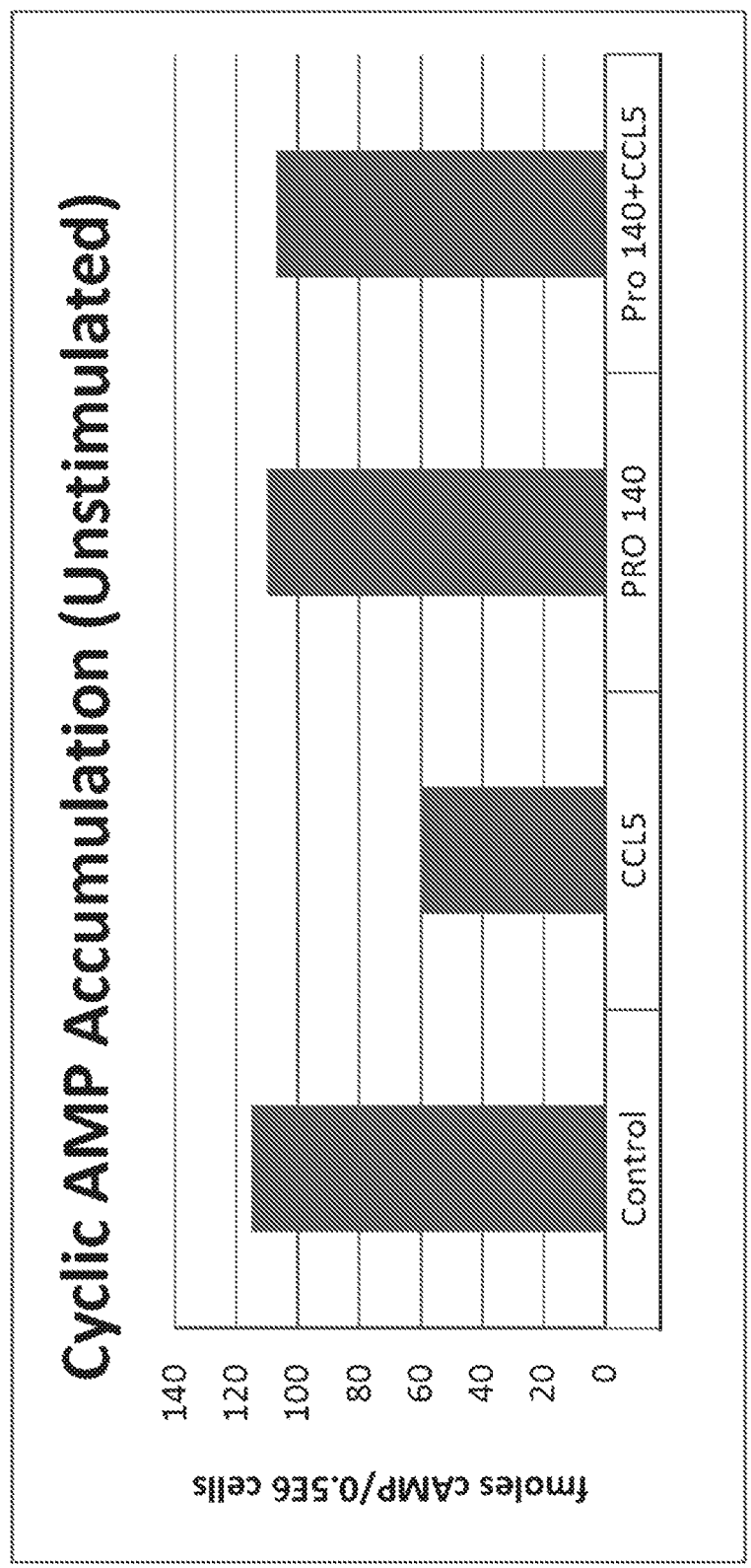
FIG. 1 shows cAMP accumulation in unstimulated cells (without addition of forskolin (FSK)) as measured in fmoles cAMP/0.5E6 cells in the presence of rolipram, i.e., basal cAMP for control cells in the presence of rolipram (control), cells in the presence of rolipram and CCL5, cells in the presence of rolipram and PRO 140, and cells in the presence of rolipram, PRO 140, and CCL5.

Here, the interface between PRO 140 (a known humanized monoclonal antibody CCR5 antagonist with anti-HIV properties) and the CCL5 ligand as such relate to CCR5 receptor binding and the resultant downstream immunomodulatory effects of such binding was studied in closer detail.

The experimental data provided here supports the role of PRO 140 in inhibiting, interrupting, blocking, mitigating, dampening, slowing the progress of, or eliminating the triggering of the downstream effects of CCL5 on CCR5 receptor positive cells. The evidence also shows that PRO 140 does not, by itself (or alone), have a CCL5 agonist effect with respect to at least some downstream immunomodulatory effects such as, for example, cAMP level decreases or cell migration induction. It is contemplated that the evidence provided here may also indicate that PRO 140 does not, by itself, have a CCL5 agonist effect with respect to other downstream immunomodulatory effects.

Accordingly, the present inventor has advantageously discovered that PRO 140 bound to CCR5 may have therapeutic potential that exceeds or surpasses other available anti-CCR5 inhibitors to the extent that it downregulates one or more downstream effects of typical CCL5 ligand and CCR5 receptor binding in the presence of the CCL5 ligand without independently stimulating or triggering downstream effects of CCL5 ligand CCR5 receptor binding. Here, it may be expected that PRO 140, any isotype of PRO 140, or a part, fragment, derivative, or conjugate of PRO 140 or a PRO 140 isotype may have similar CCR5 binding activity without having or demonstrating independent CCL5 agonist activity.

As noted above, PRO 140 and, for example, the small molecule CCR5 inhibitors such as maraviroc have distinct CCR5 binding patterns and, as shown here, distinct CCL5 stymying, inhibiting, or blocking effects. Importantly, it is demonstrated here that maraviroc, even while acting to inhibit, interrupt, block, mitigate, dampen, slow the progress of, or eliminate the triggering of the downstream effects of CCL5 on CCR5 receptor positive cells also gives rise to independent and separate CCL5 agonistic downstream CCL5/CCR5 axis signaling effects that may counteract or diminish the effectiveness of these CCR5 competitive inhibitors for the purposes of immunomodulatory regulation, alteration, or control for therapeutic purposes.

The present invention thus provides new methods of using PRO 140, any isotype of PRO 140, or a part, fragment, derivative, or conjugate of PRO 140 or a PRO 140 isotype for the therapeutic treatment of subjects in need of immunomodulatory regulation, alteration, or control. The new methods of the present invention comprise administration of competitive inhibitors to the CCR5 cell receptor that do not have CCL5 agonist activity to subjects in need of immunomodulatory therapy. The new methods of the present invention comprise methods that do not give rise to counterproductive CCL5 agonist activity upon CCLR receptor binding that results in one or both of decreased cAMP levels and increased cell migration.

In one embodiment of the present invention, the competitive inhibitor to the CCR5 cell receptor does not have agonist activity. Such a competitive inhibitor may be an antibody, protein, small molecule, or a part or fragment of an antibody, protein, small molecule, or a derivative or conjugate of any of the above. In a preferred embodiment of the present invention, the competitive inhibitor is PRO 140, or any humanized monoclonal antibody of any isotype of PRO 140, that competitively inhibits CCL5 agonist activity relating to the CCR5 receptor CCL5 ligand axis, or a part, fragment, derivative, or conjugate thereof.

In an embodiment of the present invention, the CCL5 competitive inhibitor alone has no in vitro effect on CCR5 cell receptor regulation of cAMP levels. In another embodiment, the competitive inhibitor in the presence of CCL5 in vitro or in vivo inhibits CCL5 triggered CCR5 receptor CCL5 ligand axis agonist activity as indicated or characterized by increased cAMP levels.

In an embodiment of the present invention, the CCL5 competitive inhibitor alone has no in vitro effect on cell migration. In another embodiment, the competitive inhibitor in the presence of CCL5 in vitro or in vivo inhibits induced migration triggered by CCL5/CCR5 axis activity.

The present invention also includes new methods of using a competitive inhibitor to the CCR5 cell receptor to inhibit, dampen, blunt, interrupt, block, mitigate, slow the progress of, and/or treat inflammation and/or various other CCR5/CCL5 receptor/ligand axis signaling dependent down-stream activities associated with GvHD, autoimmune disorders, infectious agents, chronic inflammation, cancer, etc. Such methods include the use or administration of a competitive inhibitor that is an antibody, protein, small molecule, or a part or fragment of an antibody, protein, small molecule, or a fragment, derivative, or conjugate of any of the above. Preferred competitive inhibitors of the present invention comprise PRO 140, or any humanized monoclonal antibody of any isotype of PRO 140, that competitively inhibits CCL5 triggered CCR5 receptor CCL5 ligand axis agonist activity, or a part, fragment, derivative, or conjugate thereof.

In a preferred embodiment, the inventive method newly uses PRO 140, or any humanized monoclonal antibody of any isotype of PRO 140, that competitively inhibits CCL5 triggered CCR5 receptor CCL5 ligand axis agonist activity, or a part, fragment, derivative, or conjugate thereof, to achieve therapeutic immunomodulation in a subject in need thereof.

The methods of the present invention include the use of a competitive inhibitor to inhibit, diminish, blunt, reduce, mask, interrupt, block, mitigate, slow the progress of, or treat GvHD.

The methods of the present invention include the use of a competitive inhibitor to inhibit, diminish, blunt, reduce, mask, interrupt, block, mitigate, slow the progress of, or treat an autoimmune disorder, including but not limited to those autoimmune disorders specified above.

The methods of the present invention include the use of a competitive inhibitor to inhibit, diminish, blunt, reduce, mask, interrupt, block, mitigate, slow the progress of, or treat an infectious agent.

The methods of the present invention include the use of a competitive inhibitor to inhibit, diminish, blunt, reduce, mask, interrupt, block, mitigate, slow the progress of, or treat chronic inflammation, including but not limited to those chronic inflammation conditions and diseases specified above.

The methods of the present invention include the use of a competitive inhibitor to inhibit, diminish, blunt, reduce, mask, interrupt, block, mitigate, slow the progress of, or treat cancer, including but not limited to those cancers specified above.

In an alternative method of the present invention, the competitive inhibitor is combined with at least a second competitive inhibitor to the CCR5 cell receptor, wherein at least the second competitive inhibitor is known to have CCL5 agonist activity, to inhibit, diminish, blunt, reduce, mask, interrupt, block, mitigate, slow the progress of, or treat inflammation and/or various other CCR5 receptor and CCL5 ligand axis signaling dependent down-stream activities associated with GvHD, autoimmune disorders, infectious agents, chronic inflammation, cancer, etc. Due to the distinct CCR5 binding patterns of the preferred competitive inhibitors of the present invention and those of certain small molecule anti-CCR5 agents, the combined use of these components may be expected to give rise to some synergistic activities and effects.

Any of the methods described herein may further comprise the steps of providing or administering the competitive inhibitor alone to a subject to alter CCR5 cell receptor regulation of cAMP levels of the subject.

Any of the methods described herein may further comprise the steps of providing or administering the competitive inhibitor to a subject to inhibit CCL5 triggered CCR5 receptor CCL5 ligand axis agonist activity, and measuring cAMP production levels. Such methods may comprise measuring a subject's cAMP production levels before, after, and/or during treatment to assess the therapeutic effectiveness of the competitive inhibitor and/or determine proper dosage and course of treatment.

Any of the methods described herein may further comprise the steps of providing or administering the competitive inhibitor by itself (alone) to a subject to down-regulate the cell migration otherwise induced by innate CCL5 ligand and CCR5 receptor binding. Any of the methods described herein may further comprise the steps of providing or administering the competitive inhibitor to a subject to down-regulate the cell migration otherwise induced by innate CCL5 ligand and CCR5 receptor binding, and measuring cell migration. Such methods may comprise measuring a subject's cell migration levels before, after, and/or during treatment to assess the therapeutic effectiveness of the competitive inhibitor and/or determine proper dosage and course of treatment.

It is contemplated that a therapeutically effective amount of the PRO 140 CCL5 competitive inhibitor of the present invention may be, for example, administered in a 350 mg subcutaneous dose split between two 175 mg/mL injections. However, as noted above, to the extent that the effects of the competitive inhibitor have been determined to be dose dependent, it is understood that the dosage amount and course of treatment may be adjusted to fit a particular subject's needs, or the needs of a particular patient group.

Experimental Data

Experiment 1: CCL5 Competitive Inhibition and Downstream cAMP

The first set of experiments was designed to see if PRO 140 has antagonist and/or agonist activity for alternative signaling pathways known to be activated downstream of CCR5 engagement, such as G-protein mediated modulation of intracellular cyclic AMP (cAMP) or specific tyrosine kinase activation.

a. Cell Lines: Primary CD4+ cell lines were prepared from healthy human donors and grown for 7-10 days prior to sorting for CD4+ CCR5+ T cells. PBMC were stimulated with 1 ug/ml of PHA-L Sigma (2E6/well in 24 well plates). PHA lines were expanded using 30 U/ml IL-2 for 24 hours after stimulation and every other day until FACS sorting for CD4+ CCR5+ T cells (on days 7-10). FACS sorting was done using anti-human CD4-percp-Cy5.5 clone RPA-T4, Mouse IgG1k, at 25 ug/ml, with a working concentration of 0.125 ug/ml. Anti-human CCR5-PE clone NP-6G4, Mouse IgG1k, concentration 25 ug/ml, working concentration 1.25 ug/ml was used.

b. Methods: Cell lines were assayed for cAMP levels in the absence or presence of rolipram (20 uM, a cyclic nucleotide phosphodiesterase-4 (PDF-4) inhibitor) with either no addition (basal cAMP) or in response to forskolin (FSK) (10 uM, a non-specific activator of cAMP synthesis), PRO 140 (1 ug/ml), forskolin+PRO 140, CCL5 (0.1 uM), CCL5+forskolin, or PRO 140+CCL5+forskolin. Incubations (0.5E6 cells/ml) were conducted at 37° C. for 10 minutes and then terminated by addition of ice-cold 7.5% trichloroacetic acid (TCA). cAMP was quantified by radioimmunoassay. Statistical significance was determined by unpaired, one-tailed t test analysis using GraphPad prism software, version 4.0 c. Results: All of the cell lines expressed basal cAMP levels and increased cAMP in response to forskolin. CCL5 decreased cAMP levels and PRO 140 had no effect on cAMP levels when used as single agents. PRO 140 diminished the effects of CCL5 on decreasing cAMP, i.e., PRO 140 reduced the CCL5 triggered decrease in cAMP levels.

FIG. 1 "Cyclic AMP Accumulation (Unstimulated)" shows cAMP accumulation as measured in fmoles cAMP/0.5E6 cells in the presence of rolipram and without addition of forskolin, i.e., basal cAMP. Control cell lines in the presence of rolipram showed cAMP accumulation measured as 115 fmoles cAMP/0.5E6 cells. Cell lines in the presence of rolipram and CCL5 showed cAMP accumulation measured as 60 fmoles cAMP/0.5E6 cells. Cell lines in the presence of rolipram and PRO 140 showed cAMP accumulation measured as 110 fmoles cAMP/0.5E6 cells. Cell lines in the presence of rolipram, PRO 140, and CCL5 showed cAMP accumulation measured as 107 fmoles cAMP/0.5E6 cells.

Figure 2:
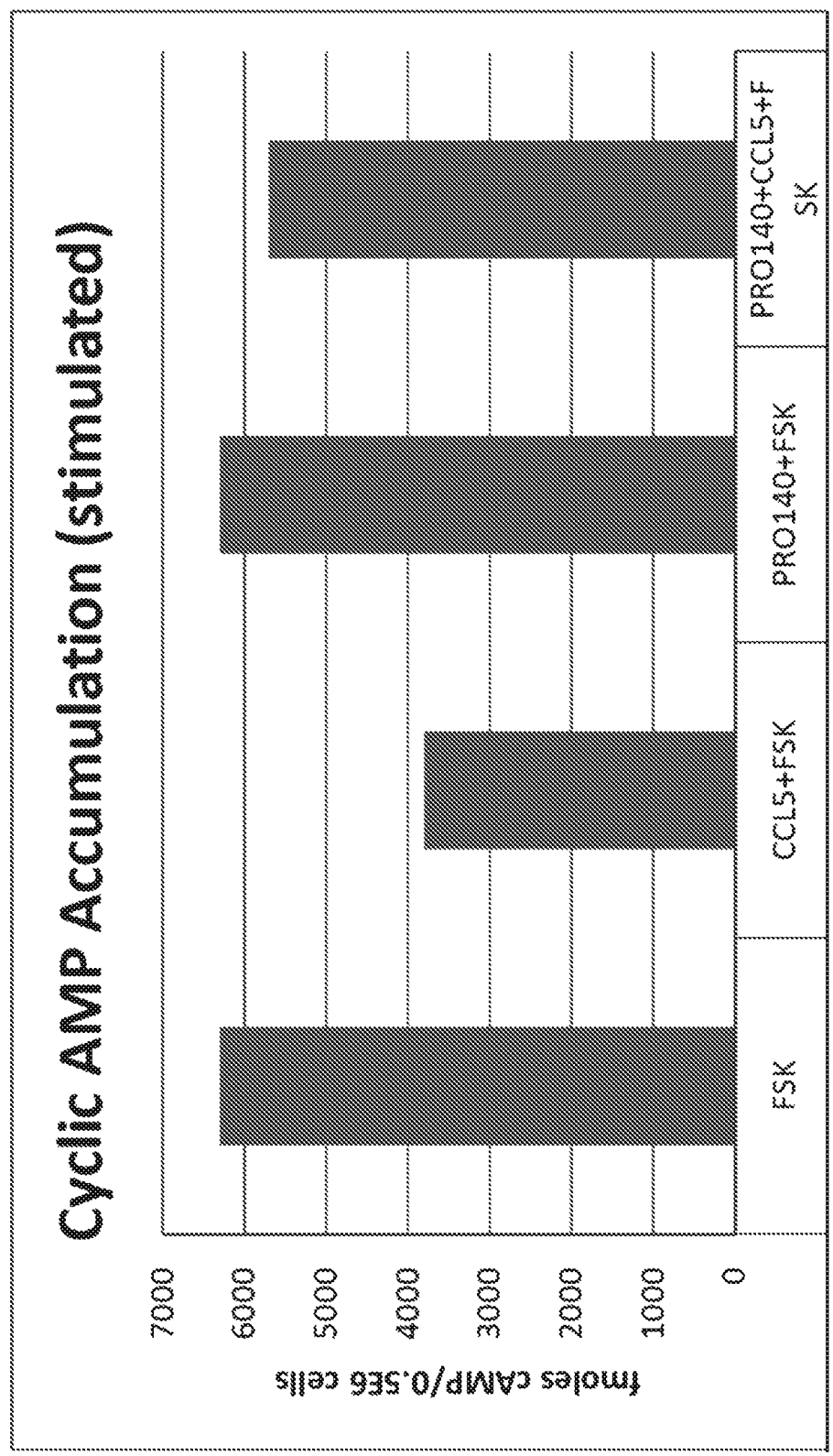
FIG. 2 shows cAMP accumulation in stimulated cells (with addition of forskolin (FSK)) as measured in fmoles cAMP/0.5E6 cells in the presence of rolipram and FSK (control), cells in the presence of rolipram, CCL5, and FSK, cells in the presence of rolipram, PRO 140, and FSK, and cells in the presence of rolipram, PRO 140, CCL5, and FSK.

FIG. 2 "Cyclic AMP Accumulation (Stimulated)" shows cAMP accumulation as measured in fmoles cAMP/0.5E6 cells in the presence of rolipram and with the addition of forskolin (FSK). Control cell lines in the presence of rolipram FSK and showed cAMP accumulation measured as 6300 fmoles cAMP/0.5E6 cells. Cell lines in the presence of rolipram, CCL5, and FSK showed cAMP accumulation measured as 3800 fmoles cAMP/0.5E6 cells. Cell lines in the presence of rolipram, PRO 140, and FSK showed cAMP accumulation measured as 6300 fmoles cAMP/0.5E6 cells. Cell lines in the presence of rolipram, PRO 140, CCL5, and FSK showed cAMP accumulation measured as 5700 fmoles cAMP/0.5E6 cells.

Figure 3:
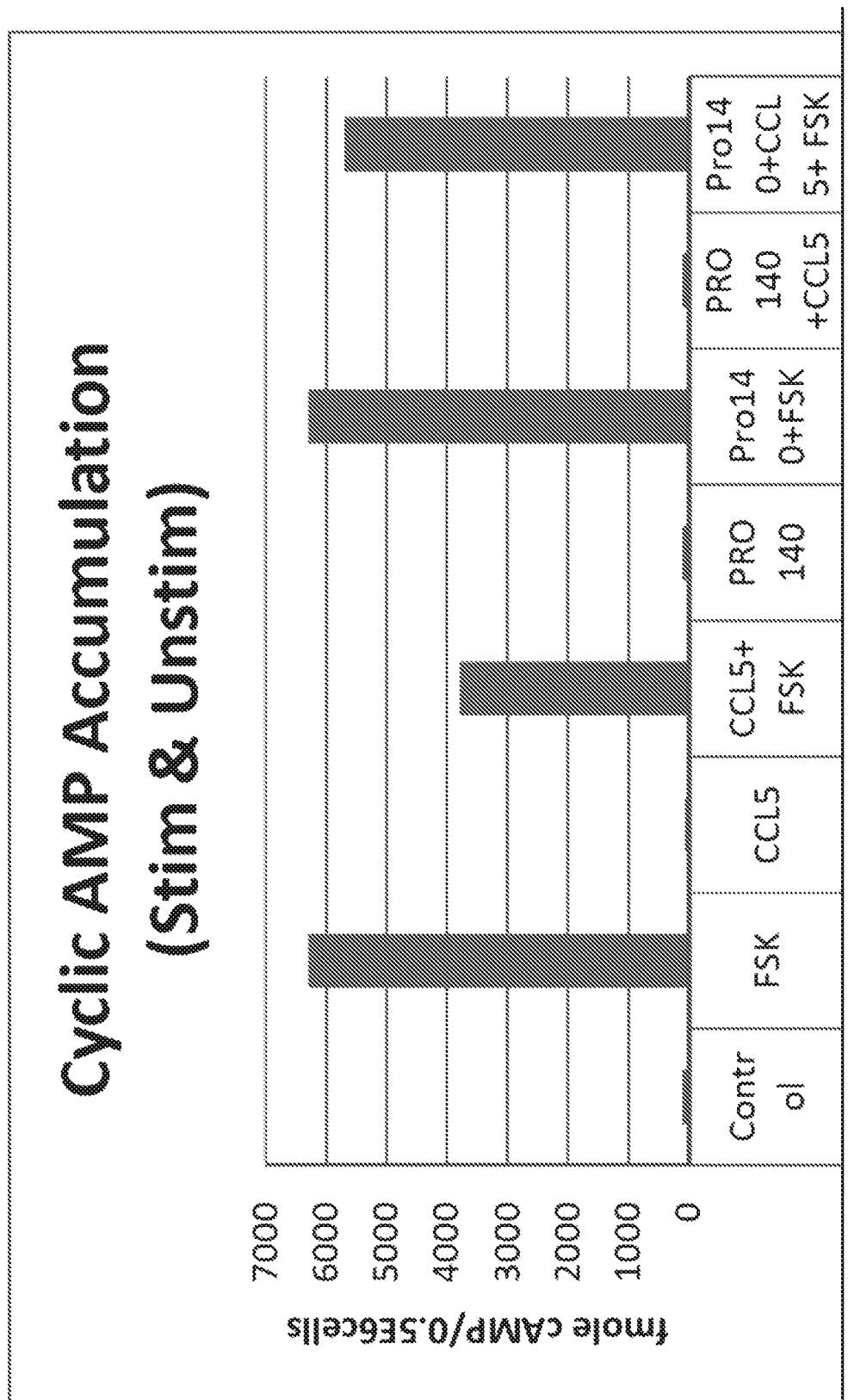
FIG. 3 combines the data of FIG. 1 and FIG. 2 and shows cAMP accumulation in unstimulated and stimulated cells.

FIG. 3 "Cyclic AMP Accumulation (Stimulated)" combines the data of FIG. 1 and FIG. 2.

d. Conclusion: PRO 140 has no direct effect (agonist activity) on cAMP formation in CD4+ cells but instead is an inhibitor of the action of CCL5 as a CCR5 agonist, to decrease cAMP levels in such cells. That is, PRO 140 inhibits CCL5 decreased cAMP levels in CD4+ cells.

Experiment 2: CCL5 Competitive Inhibition and Chemotaxis

Figure 4:
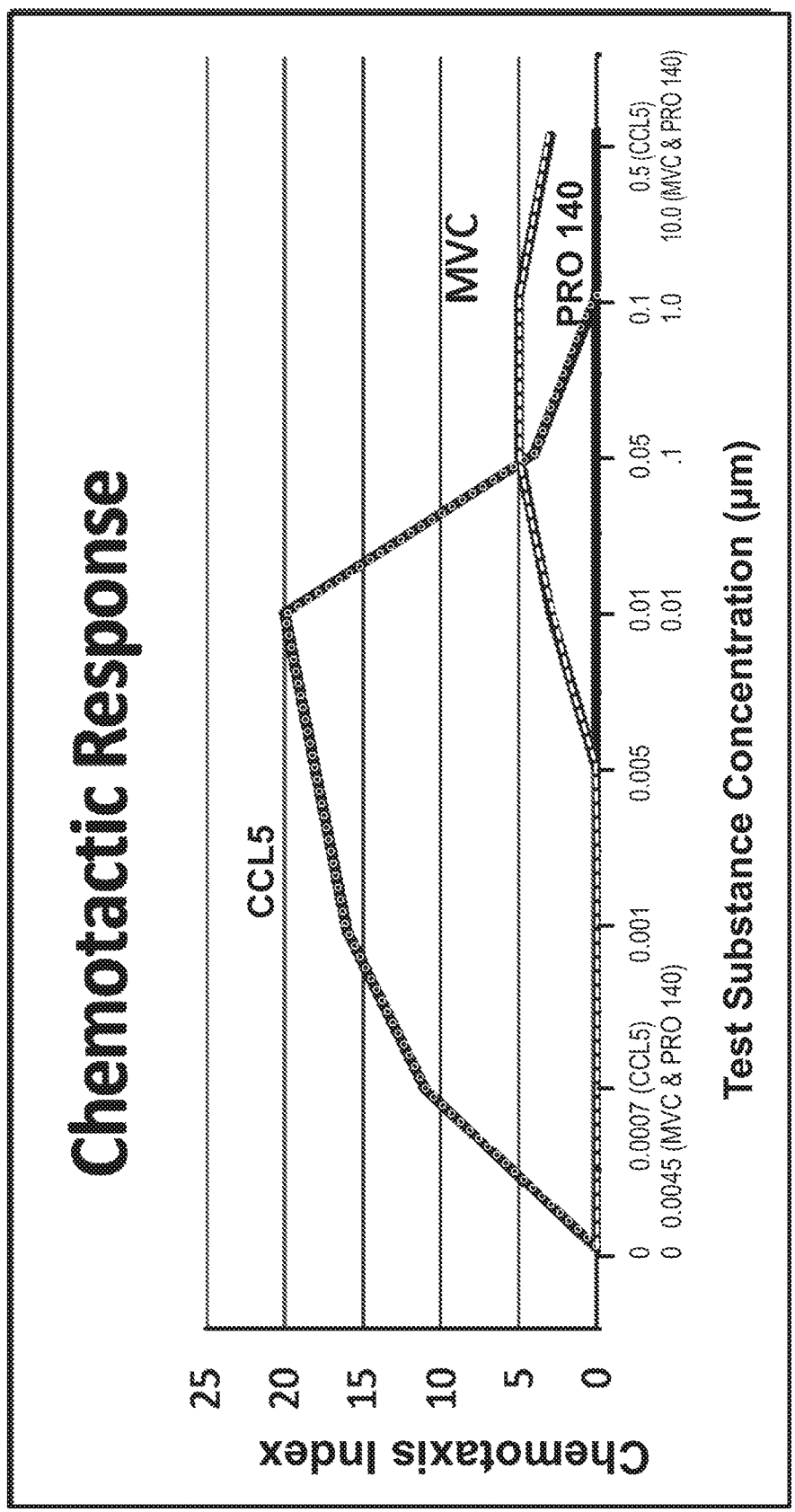
FIG. 4 show the chemotactic response of each of CCL5, PRO 140, and maraviroc.

This experiment was designed to investigate the role of PRO 140 on chemotaxis induced by CCL5 engagement of the CCR5 receptor on CHO-CCR5 target cells (CHO-K1 cell line).

a. Cell Lines: The CHO-K1 cell line was transfected with a human CCR5 expression plasmid and selected for expression. Production of the full length protein was confirmed by western blot. Fluorescence-activated cell sorting (FACS) analysis was used to sort for cells that expressed CCR5 on the surface and these cells were purified and expanded.

b. Methods: Migration assays were done in Multiscreen MC plates using CHO-K1-hCCR5 cells in the upper chamber and with media and test agents in the bottom chamber. The agents tested included: PRO 140, Maraviroc (MVC), CCL5, forskolin (FSK), and an IgG4 control as single agents, and PRO 140+CCL5, and Maraviroc+CCL5 as combined agents. The effects on the Chemotaxis Index were measured over a wide concentration range of the test substance. The Chemotaxis Index was calculated as the migration of cells into the lower chamber with a test substance divided by the migration of cells into the lower chamber without the test substance or with a control substance. Migration was measured using the ATPlite assay. All assays were performed in triplicate. Data analysis was determined by the Chemotaxis Index over a wide concentration range of the test substance. Dose ranges of test agents were as follows: PRO 140 was 0.0045-10 ug/ml; MVC was 0.0045-10 µM; CCL5 was 0.0007-0.50 µM; FSK was 0.0045-10 µM; IgG4 control was 0.0045-10 µg/ml.

c. Results: FIG. 4 titled "Chemotactic Response" compares the chemotactic response of cells in the presence of just PRO 140, MVC, and CCL5. The chemotactic response of PRO 140 was undetectable (Chemotaxis Index=0) over the wide concentration range (0.0045-10 µg/ml) tested (y-axis). The chemotactic response of MVC was significant over a concentration range above 0.01 µM. The chemotactic response of CCL5 was pronounced over a wide concentration range (0.0007-0.50 µM) but dropped off at very high concentrations.

Figure 5:
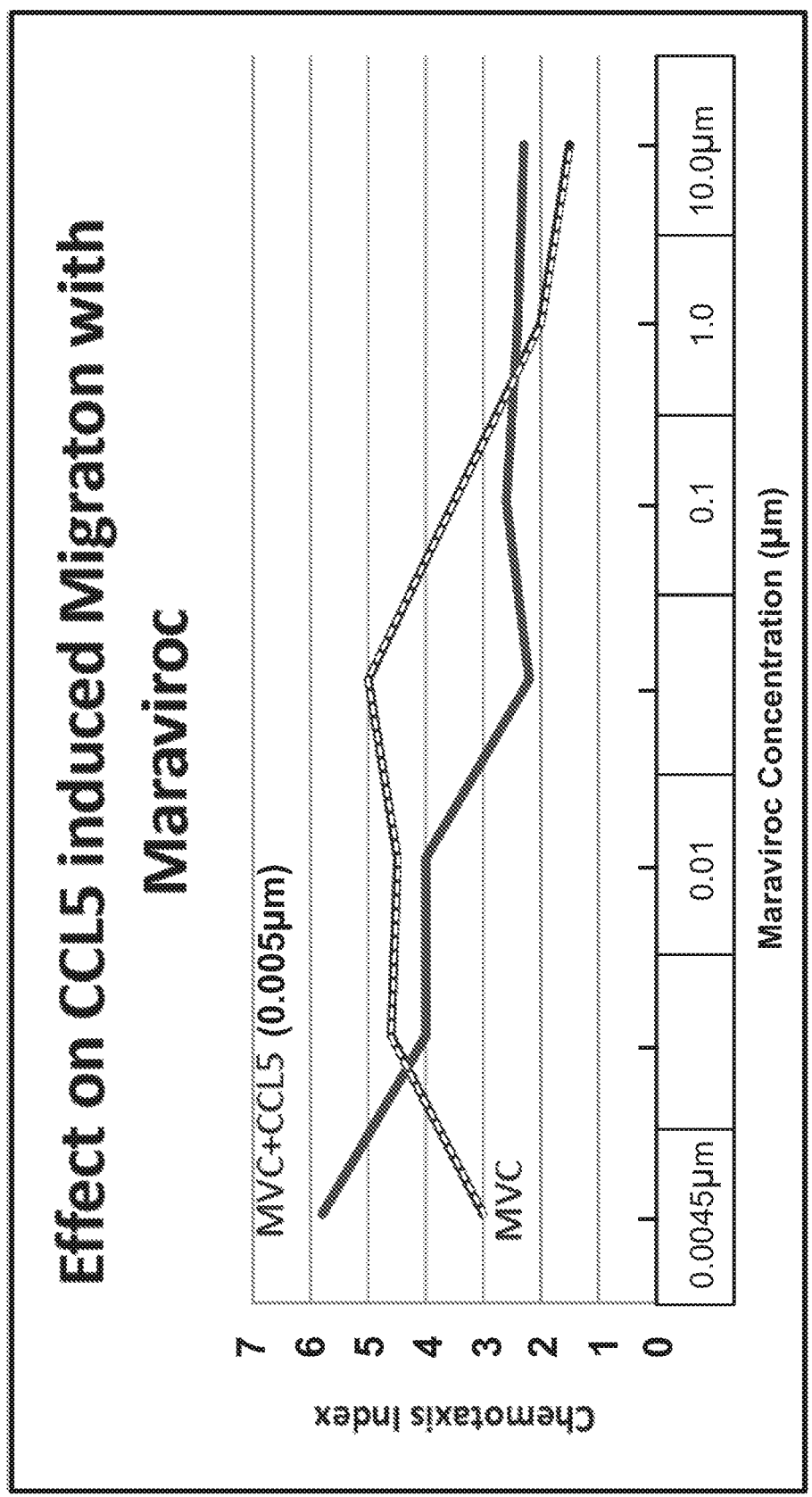
FIG. 5 shows the effect of CCL5 induced migration with maraviroc in the presence or absence of CCL5.

FIG. 5 titled "Effect of CCL5 induced migration with Maraviroc" compares cell migration in the presence of Maraviroc (MVC) alone over a wide concentration range (0.0045-10 µM) and the ability of MVC to inhibit the migration induced by a constant dose of CCL5 (0.005 µM). MVC inhibited CCL5 induced migration at concentrations above 0.05 µM but also expressed significant direct induction of migration on its own over a wide concentration range.

Figure 6:
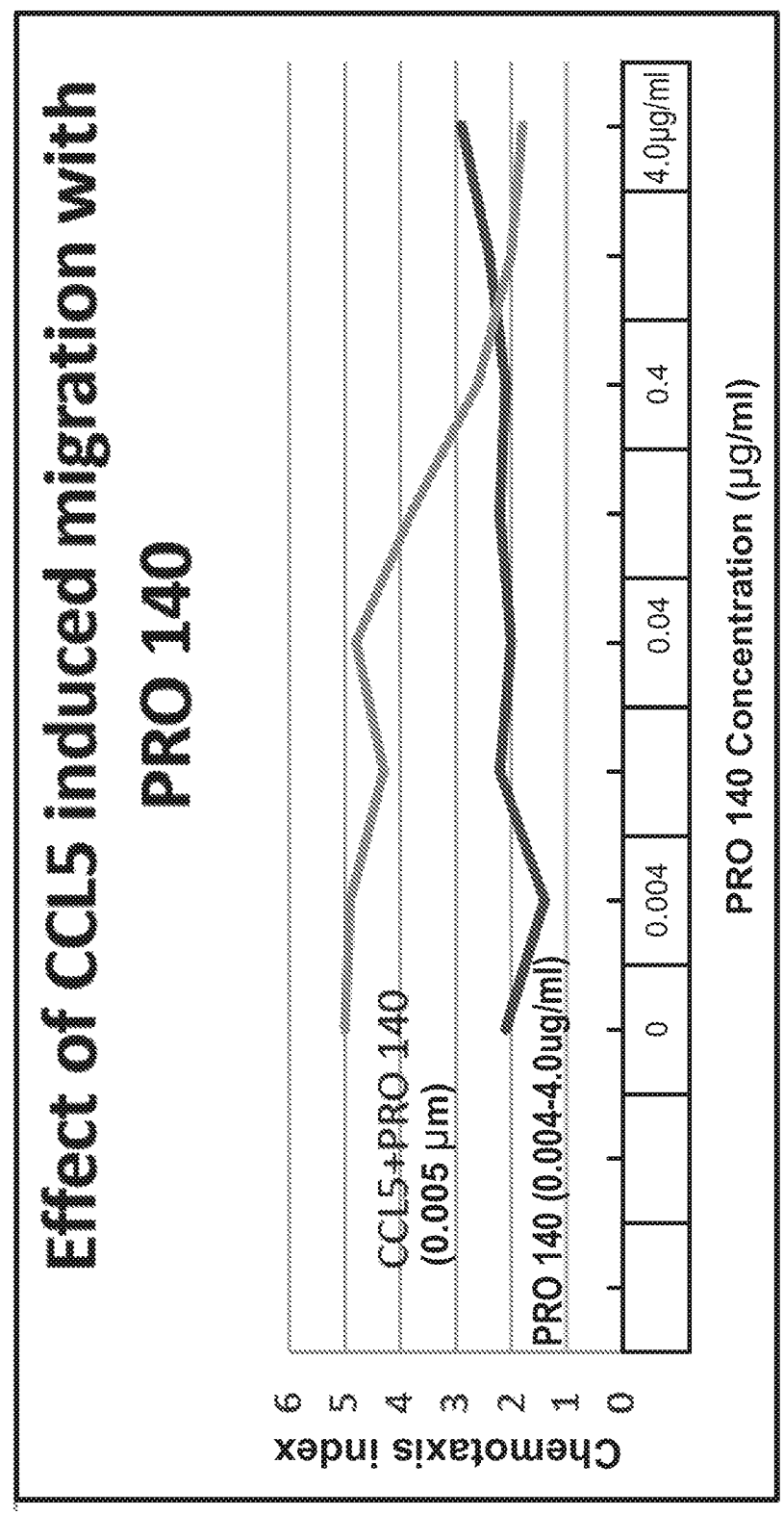
FIG. 6 shows the effect of CCL5 induced migration with PRO 140 in the presence or absence of CCL5.

FIG. 6 titled "Effect of CCL5 induced migration with PRO 140" compares cell migration in the presence of PRO 140 alone over a wide concentration range (0.0045-4.0 µg/ml) and the ability of PRO 140 to inhibit the migration induced by a constant dose of CCL5 (0.005 µM). PRO 140 on its own did not result in any significant migration (Chemotaxis Index less than 3) over a wide concentration range. In the higher concentration ranges of PRO 140 (e.g., above 0.4 µg/ml) the migration induced by CCL5 was inhibited by PRO 140.

d. Conclusion: PRO 140 by itself did not have an effect on migration (chemotaxis). CCL5 induced migration was inhibited by MVC. But MCV also produced agonist activity on its own by stimulating migration. PRO 140 inhibited the induced migration by CCL5.

PRO 140 has no direct effect (agonist activity) on cell migration (chemotaxis) but instead is an inhibitor of the effects of CCL5-induced migration (antagonist activity). MVC showed both agonist and antagonist activity on CCL5 engagement of CCR5 chemotaxis.

The invention claimed is:
1. A method of treating graft versus host disease in a subject in need of CCR5 receptor signaling immunomodulatory intervention comprising: administering a competitive inhibitor to the CCR5 cell receptor that does not itself have

CCL5 agonist activity, wherein administering the competitive inhibitor reduces CCL5 ligand and CCR5 receptor signaling in the subject;
    testing the subject to measure the immunomodulation of CCL5 binding to CCR5 receptor induced cAMP levels triggered by administration of the competitive inhibitor;
  monitoring cAMP production levels of the test subject before, after, or during treatment to assess the therapeutic effectiveness of the competitive inhibitor; and
wherein the competitive inhibitor consists of PRO 140.

2. The method of claim 1, wherein the competitive inhibitor results in increased cAMP levels in the subject.

3. The method of claim 1, wherein the competitive inhibitor reduces cell migration in the subject.

4. The method of claim 1, further comprising adjusting a dose amount of the competitive inhibitor to achieve down-regulation of CCL5 induced cell migration.

5. The method of claim 1, further comprising administering a second competitive inhibitor to the CCR5 cell receptor.

6. The method of claim 1, further comprising supplementing immunomodulatory intervention with maraviroc with PRO 140, wherein the subject was previously treated with maraviroc.

7. The method of claim 1, wherein treating the subject with PRO 140 prevents the development or progression of, or reduces the inflammation in, a subject with graft versus host disease.

8. A method of treating a subject with PRO 140 consisting of:
  administering PRO 140 to a subject;
  competitively inhibiting CCL5 ligand bound to CCR5 receptor activity, wherein administering the PRO 140 reduces CCL5 ligand and CCR5 receptor signaling;
  testing the subject to measure the immunomodulation of CCL5 binding to CCR5 receptor induced cAMP levels triggered by administration of the PRO 140, wherein the PRO140 inhibits a decrease of CCL5 binding to CCR5 receptor induced cAMP levels;
  monitoring cAMP production levels of the test subject before, after, or during treatment to assess the therapeutic effectiveness of the PRO 140; and
  wherein administering the PRO 140 treats inflammation associated with GVHD.

9. The method of claim 8, wherein the competitive inhibitor results in increased cAMP levels in the subject.

10. The method of claim 8, wherein the competitive inhibitor reduces cell migration in the subject.

11. The method of claim 8, wherein a dose amount of the competitive inhibitor achieves down-regulation of CCL5 induced cell migration.

* * * * *